United States Patent [19]

Keil et al.

[11] Patent Number: 4,659,367
[45] Date of Patent: Apr. 21, 1987

[54] CYCLOHEXENONE DERIVATIVES AND THEIR USE FOR CONTROLLING UNDESIRABLE PLANT GROWTH

[75] Inventors: Michael Keil, Freinsheim; Dieter Jahn, Edingen-Neckarhausen; Rainer Becker, Bad Durkheim; Norbert Goetz, Worms; Bruno Wuerzer, Otterstadt; Norbert Meyer, Ladenburg, all of Fed. Rep. of Germany

[73] Assignee: BASF Aktiengesellschaft, Fed. Rep. of Germany

[21] Appl. No.: 679,243

[22] Filed: Dec. 7, 1984

[30] Foreign Application Priority Data

Dec. 8, 1983 [DE] Fed. Rep. of Germany ....... 3344352
Aug. 10, 1984 [DE] Fed. Rep. of Germany ....... 3429437

[51] Int. Cl.$^4$ .................. A01N 43/02; C07D 333/22; C07D 333/02
[52] U.S. Cl. .......................... 91/90; 71/91; 549/77
[58] Field of Search ....... 549/13, 28, 75, 77; 71/90, 91, 88

[56] References Cited

U.S. PATENT DOCUMENTS 3,989,737 11/1976 Sawaki et al. ............ 549/75
4,432,786 2/1984 Loh ........................... 549/75

FOREIGN PATENT DOCUMENTS 0070370 5/1982 European Pat. Off. .
0115808 1/1984 European Pat. Off. .
0062248 4/1982 Japan ....................... 549/75

Primary Examiner—Nicky Chan
Attorney, Agent, or Firm—Keil & Weinkauf

[57] ABSTRACT

Cyclohexenone derivatives of the formula

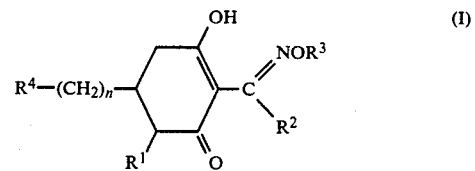

where $R^1$ is hydrogen or alkoxycarbonyl, $R^2$ is alkyl, $R^3$ is alkyl, alkenyl, alkynyl or haloalkenyl, $R^4$ is a non-aromatic 5-membered ring which may or may not contain a double bond and contains a sulfur atom or a sulfinyl or sulfonyl group as a ring member, and n in 0, 1 or 2, are used for controlling undesirable plant growth.

14 Claims, No Drawings

CYCLOHEXENONE DERIVATIVES AND THEIR USE FOR CONTROLLING UNDESIRABLE PLANT GROWTH

The present invention relates to novel cyclohexenone derivatives, and herbicides which contain these compounds as active ingredients.

EP-A-00 71 707 discloses that a number of cyclohexenones which are substituted in the 5-position by certain non-aromatic heterocycles are herbicides.

We have found that cyclohexenone derivatives of the formula

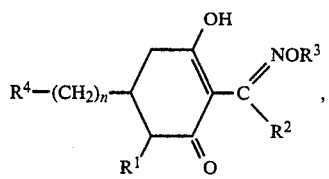

where $R^1$ is hydrogen or alkoxycarbonyl of 2 to 5 carbon atoms, $R^2$ is alkyl of 1 to 4 carbon atoms, $R^3$ is alkyl of 1 to 4 carbon atoms, alkenyl of 3 or 4 carbon atoms, alkynyl of 3 or 4 carbon atoms or haloalkenyl of 3 or 4 carbon atoms and 1 to 3 halogen atoms, $R^4$ is a non-aromatic 5-membered ring which may or may not contain a double bond, contains a sulfur atom or a sulfinyl or sulfonyl group, as a ring member and is unsubstituted or substituted by 1, 2 or 3 alkyl groups of 1 to 4 carbon atoms, and n is 0, 1 or 2, with the proviso that n is not 0 when $R^4$ is a 5-membered ring containing a sulfinyl or sulfonyl group, and salts of these compounds possess herbicidal activity.

The cyclohexenone derivatives of the formula I can occur in a plurality of forms, all of which are embraced by the claim:

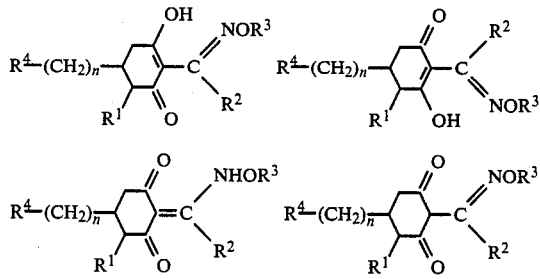

In formula I, $R^1$ is hydrogen or alkoxycarbonyl of 1 to 4 carbon atoms, in particular methoxycarbonyl, $R^2$ is straight-chain or branched alkyl of 1 to 4 carbon atoms, ie. methyl, ethyl, n-propyl, isopropyl, n-butyl, sec.-butyl, isobutyl or tert.-butyl, $R^3$ is propargyl, alkyl of 1 to 4 carbon atoms, alkenyl of 3 or 4 carbon atoms or haloalkenyl of 3 or 4 carbon atoms which can contain not more than three halogen substituents, eg. methyl, ethyl, n-propyl, isopropyl, n-butyl, sec.-butyl, isobutyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl, and $R^4$ is a non-aromatic 5-membered ring which may or may not contain a double bond, contains a sulfur atom or a sulfinyl or sulfonyl group as a ring member and is unsubstituted or substituted by 1, 2 or 3 alkyl groups of 1 to 4 carbon atoms, preferably methyl, ethyl or n-propyl. Examples of $R^4$ are tetrahydrothienyl, 2,5-dihydrothienyl, 1-oxotetrahydrothienyl, 1-oxo-2,5-dihydrothienhl, 1,1-dioxo-2,5-dihydrothienyl or 1,1-dioxotetrahydrothienyl, eg. tetrahydrothien-3-yl, 2,5-dihydrothien-3-yl, 1-oxotetrahydrothien-3-yl, 2,5-dihydro-1-oxothien-3-yl, 1,1-dioxotetrahydrothien-3-yl, 2,5-dihydro-1,1-dioxothien-3-yl, 2-methyltetrahydrothien-3-yl, 2,5-dihydro-2-methyl-1-oxothien-3-yl, 2,2-dimethyltetrahydrothien-3-yl, 2,5-dihydro-2,2-dimethylthien-3-yl, 2,2-dimethyl-1-oxo-tetrahydrothien-3-yl, 2,5-dihydro-2,2-dimethyl-1-oxothien-3-yl, 2,2-dimethyl-1,1-dioxotetrahydrothien-3-yl, 2,5-dihydro-2,2-dimethyl-1,1-dioxothien-3-yl, tetrahydrothien-2-yl, 1-oxotetrahydrothien-2-yl, 1,1-dioxotetrahydrothien-2-yl, 4,5-dihydro-4-methylthien-2-yl, 4,5-dihydro-4-methyl-1-oxotthien-2-yl, 4,5-dihydro-1,1-dioxo-4-methylthien-2-yl, 4-methyltetrahydrothien-2-yl, 4-methyl-1-oxotetrahydrothien-2-yl, 4-methyl-1,1-dioxotetrahydrothien-2-yl, 4,5-dihydro-4,5-dimethylthien-2-yl, 4,5-dihydro-4,5-dimethyl-1-oxothien-2-yl, 4,5-dihydro-4,5-dimethyl-1,1-dioxothien-2-yl, 4,5-dimethyltetrahydrothien-2-yl, 4,5-dimethyl-1-oxotetrahydrothien-2-yl, 4,5-dimethyl-1,1-dioxotetrahydrothien-2-yl, 4,5-dihydro-4-ethyl-5-n-propylthien-2-yl, 4,5-dihydro-4-ethyl-1-oxo-5-n-propylthien-2-yl, 4,5-dihydro-1,1-dioxo-4-ethyl-5-n-propylthien-2-yl, 4-ethyl-5-n-propyltetrahydrothien-2-yl, 4-ethyl-1-oxo-5-n-propyltetrahydrothien-2-yl and 1,1-dioxo-4-ethyl-5-n-propyltetrahydrothien-2-yl.

Examples of suitable salts of the compounds of the formula I are the alkali metal salts, in particular the potassium and sodium salts, the alkaline earth metal salts, in particular calcium, magnesium and barium salts, manganese, copper, zinc and iron salts, and ammonium, phosphonium, sulfonium and sulfoxonium salts, eg. ammonium, tetraalkylammonium, benzyltrialkylammonium, trialkylsulfonium or trialkylsulfoxonium salts.

The cyclohexenone derivatives of the formula I can be obtained by reacting a compound of the formula

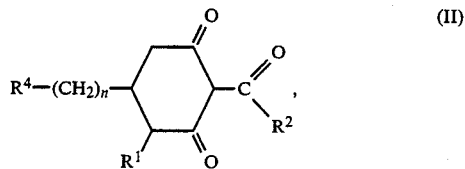

where $R^1$, $R^2$, $R^4$ and n have the abovementioned meanings, with an ammonium compound of the formula $R^3O—NH_3Y$, where $R^3$ has the above meaning and Y is an anion.

The reaction is advantageously carried out in the heterogeneous phase in an inert diluent at from 0° to 80° C., or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction takes place particularly readily at a pH of from 2 to 9, the pH advantageously being established by adding an acetate, for example an alkali metal acetate, in particular sodium acetate or potassium acetate or a mixture of the two salts. Alkali metal acetates are added, for example, in amounts of from 0.5 to 2 moles, based on the ammonia compound of the formula $R^3O—NH_3Y$.

Examples of suitable solvents are dimethyl sulfoxide, alcohols, such as methanol, ethanol or isopropanol, benene, toluene, hydrocabons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, such as methylene chloride, and distilling off the solvent under reduced pressure.

The compounds of the formula I can also be obtained by reacting a compound of the formula II with a hydroxylamine of the formula $R^3O-NH_2$, where $R^3$ has the above meanings, in an inert diluent at from 0° to the boiling point of the reaction mixture, in particular from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol, acetone or toluene. Instead of the hydroxides, it is also possible to use a sodium or potassium alcoholate for the preparation of the alkali metal salts.

The remaining metal salts, eg. the manganese, copper, zinc, iron, calcium, magnesium and barium salts, can be prepared from the sodium salts by reaction with the corresponding metal chlorides in aqueous solution. Ammonium and phosphonium salts can be obtained by reacting a compound of the formula I with an ammonium, phosphonium, sulfonium or sulfoxonium hydroxide, if necessary in aqueous solution.

The compounds of the formula II can be prepared, by a conventional method (Tetrahedron Lett. 29 (1975), 2491), from cyclohexane-1,3-diones of the formula III, which can also occur in the tautomeric forms of the formulae IIIa and IIIb

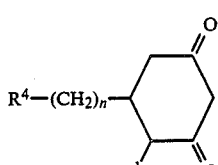

(III)

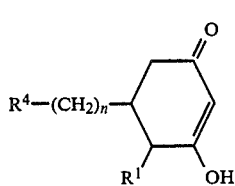

(IIIa)

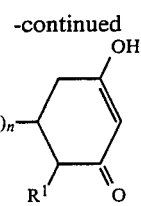

(IIIb)

It is also possible to prepare compounds of the formula II via the enol-ester intermediates which are obtained, possibly as isomer mixtures, in the conversion of compounds of the formula II, and undergo a rearrangement reaction in the presence of an imidazole or pyridine derivative (Japanese Preliminary Published Application 79/063052).

The compounds of the formula III are obtained by a conventional method, as shown in the equations below:

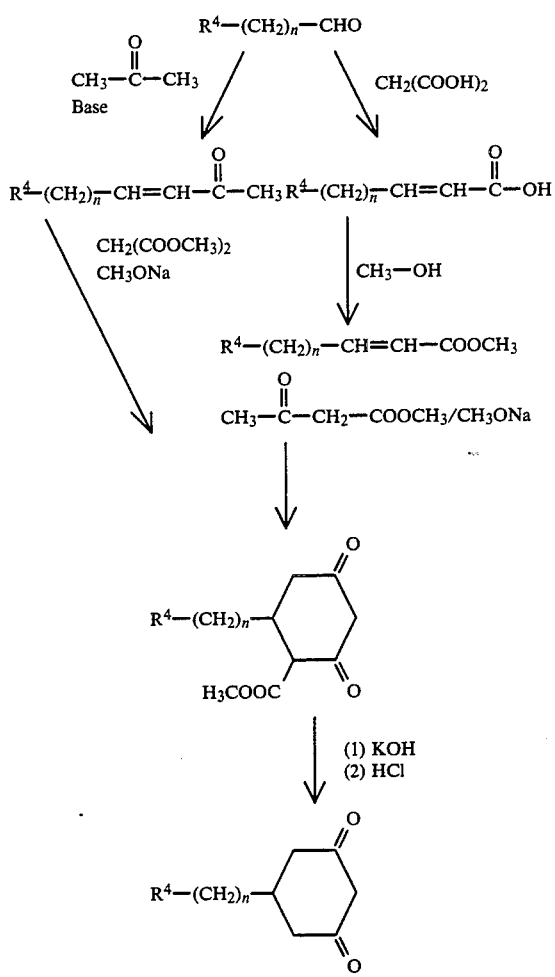

Not all of the aldehydes $R^4-(CH_2)_n-CHO$ required as starting compounds are known from the literature; they are obtained by well-known methods, for example by reduction of carboxylic acid derivatives and nitriles, Grignard reactions, hydrolysis and decarboxylation of glycidyl esters, reaction with Wittig reagents and methyl methylthiomethyl sulfoxide, or cleavage of suitable epoxides or acetals. Substitution, condensation or reduction of suitable intermediates was also successful, as the Examples below demonstrate:

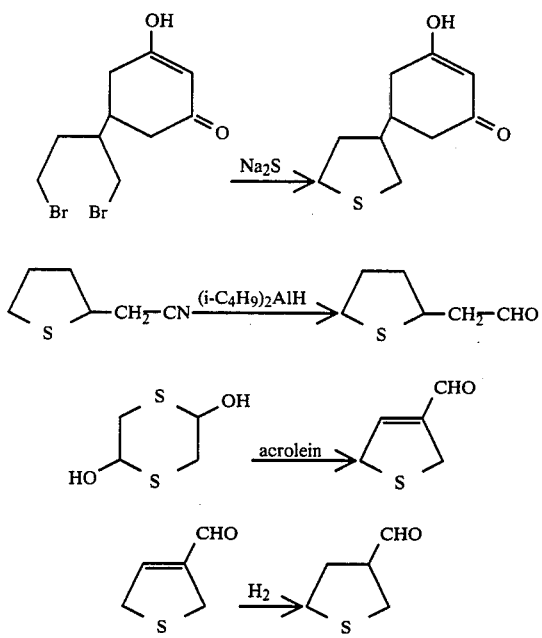

For example, tetrahydrothien-3-yl acetaldehyde is obtained in the following manner: 8.0 g of tetrahydrothien-2-yl acetonitrile (Bull. Soc. Chim. France 1974, 590) in 80 ml of absolute toluene are initially taken, and 58 ml of a 20% strength solution of diisobutylammonium hydride in toluene are added dropwise at −70° C. under a nitrogen atmosphere. Stirring is carried out for 30 minutes at −60° C., after which the reaction mixture is allowed to reach room temperature, and about 8 ml of methanol are carefully added dropwise with external cooling. Stirring is continued for 1 hour, after which the mixture is stirred into 400 ml of saturated ammonium chloride solution, and 250 ml of 5% strength sulfuric acid are added. The organic phase is separated off, extracted twice with water, dried over sodium sulfate and evaporated down, and the residue is distilled at 40°–42° C./0.4 mbar to give 3.7 g of tetrahydrothien-3-ylacetaldehyde as a clear liquid.

The compounds of the formula I can also be obtained by oxidation of an appropriate intermediate in which the sulfur has a lower oxidation state. Examples of oxidizing agents are oxyen, ozone, peroxy compounds, such as hydrogen peroxides, peracids or hydroperoxides, halogens, inorganic halogen compounds, such as a hypochlorite or a chlorate, nitrogen compounds, such as nitric acid or nitrogen pentoxide, and salts of metals having a relatively high valency, such as lead, bismuth, vanadium, manganese, chromium or cobalt salts. Anodic oxidation is also possible. The oxidation can be carried out not just to the oxime-ether stage, but in principle to any stage of the synthesis route described above.

Identification and characterization of the compounds of the formula I are most suitably carried out by means of proton nuclear resonance spectroscopy. In the Examples below, some specific $^1$H-NMR data are therefore given (solvent: CDCl$_3$; internal standard: tetramethylsilane; s=singlet, d=doublet, t=triplet, q=quartet, m=multiplet).

The Examples which follow illustrate the preparation of the cyclohexenone derivatives of the formula I.

EXAMPLE 1

4.2 g of 2-butyryl-5-(2,5-dihydro-2,2-dimethylthien-3-yl)-3-hydroxycyclohex-2-en-1-one, 1.6 g of ethoxyammonium chloride, 1.3 g of sodium bicarbonate and 50 ml of methanol are stirred at room temperature for 16 hours. The solvent is distilled off under reduced pressure, 50 ml of water and 50 ml of dichloromethane are added to the remaining residue, and the mixture is stirred, after which the phases are separated, the organic phase is dried over sodium sulfate, and the solvent is distilled off under reduced pressure to give 3.5 g of 5-(2,5-dihydro-2,2-dimethylthien-3-yl)-2-(1-ethoxyiminobutyl)-3-hydroxycyclohex-2-en-1-one as a yellowish oil.

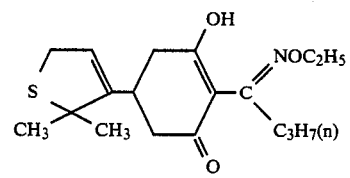

δ(ppm): 1.51 (s, 6H); 3.68 (d, 2H); 4.15 (q 2H), 5.63 (t, 1H).

EXAMPLE 2

3.0 g of 2-(1-ethoximinobutyl)-3-hydroxy-5-(tetrahydrothien-2-ylmethyl)-cyclohex-2-en-1-one are dissolved in 200 ml of chloroform, and a solution of 3.8 g of 85% strength m-chloroperbenzoic acid is added dropwise to this solution at 5° C. The reaction mixture is allowed to reach room temperature, filtered off under suction from the precipitate formed, and extracted with semisaturated sodium bicarbonate solution. The organic phase is dried over sodium sulfate, the solvent is distilled off under reduced pressure, the remaining residue is taken up in toluene, the solution is extracted with 10% strength sodium hydroxide solution, and the aqueous phase is separated off and brought to pH 4 wit dilute hydrochloric acid. Extracting with methylene chloride and evaporating down the organic phase give 5-(1,1-dioxotetrahydrothien-2-ylmethyl)-2-(1-ethoximinobutyl)-3-hydroxycyclohex-2-en-1-one.

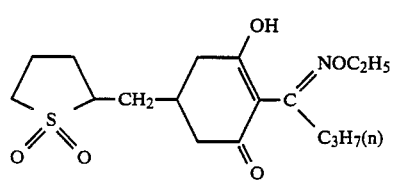

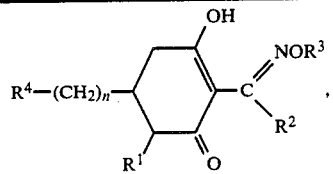

(I)

| No. | R⁴ | n | R¹ | R² | R³ | ¹H—NMR (ppm) |
|---|---|---|---|---|---|---|
| 1 | tetrahydrothien-3-yl | 0 | H | n-$C_3H_7$ | $C_2H_5$ | 0.97(t,3H); 1.33(t,3H); 2.91(m,4H); 4.12(q,2H) |
| 2 | tetrahydrothien-3-yl | 0 | H | n-$C_3H_7$ | $CH_2-CH=CH_2$ | 0.97(t,3H); 2.92(m,4H); 4.55(d,2H); 5.34(m,2H); 5.97(m,1H) |
| 3 | tetrahydrothien-3-yl | 0 | H | $C_2H_5$ | $CH_2-CH=CH_2$ | 1.13(t,3H); 2.92(m,4H); 4.54(d,2H); 5.35(m,2H); 5.97(m,1H) |
| 4 | tetrahydrothien-3-yl | 0 | H | $C_2H_5$ | $C_2H_5$ | 1.14(t,3H); 1.33(t,3H); 2.95(m,4H); 4.11(q,2H) |
| 5 | tetrahydrothien-3-yl | 0 | H | $CH_3$ | $C_2H_5$ | |
| 6 | tetrahydrothien-3-yl | 0 | H | $CH_3$ | n-$C_3H_7$ | |
| 7 | tetrahydrothien-3-yl | 0 | H | n-$C_3H_7$ | n-$C_3H_7$ | 0.97(t,3H); 2.98(m,4H); 4.00(t,2H) |
| 8 | tetrahydrothien-3-yl | 0 | H | n-$C_3H_7$ | $CH_2-C\equiv CH$ | 0.97(t,3H); 2.51(s,1H); 4.34(s,1H) |
| 9 | tetrahydrothien-3-yl | 0 | H | n-$C_3H_7$ | $CH_2-CH=CHCl$ (trans) | 0.97(t,3H); 2.95(m,4H); 4.52(d,2H); 6.10(m,1H); 6.35(d,1H) |
| 10 | tetrahydrothien-3-yl | 0 | H | n-$C_3H_7$ | $CH_2-CCl=CCl_2$ | 0.97(t,3H); 2.95(m,4H); 4.94(s,2H) |
| 11 | tetrahydrothien-3-yl | 0 | $COOCH_3$ | n-$C_3H_7$ | $C_2H_5$ | |
| 12 | tetrahydrothien-3-yl | 0 | $COOCH_3$ | n-$C_3H_7$ | $CH_2-CH=CH_2$ | |
| 13 | tetrahydrothien-3-yl | 0 | $COOCH_3$ | $C_2H_5$ | $CH_2-CH=CH_2$ | |
| 14 | tetrahydrothien-3-yl | 0 | $COOCH_3$ | $C_2H_5$ | $C_2H_5$ | |
| 15 | tetrahydrothien-3-yl | 1 | H | n-$C_3H_7$ | $C_2H_5$ | |
| 16 | tetrahydrothien-3-yl | 1 | H | n-$C_3H_7$ | $CH_2-CH=CH_2$ | |
| 17 | tetrahydrothien-3-yl | 1 | H | $C_2H_5$ | $CH_2-CH=CH_2$ | |
| 18 | tetrahydrothien-3-yl | 1 | H | $C_2H_5$ | $C_2H_5$ | |
| 19 | 2,5-dihydrothien-3-yl | 0 | H | n-$C_3H_7$ | $C_2H_5$ | 0.97(t,3H); 1.32(t,3H); 4.10(q,2H); 5.60(1H) |
| 20 | 2,5-dihydrothien-3-yl | 0 | H | n-$C_3H_7$ | $CH_2-CH=CH_2$ | |
| 21 | 2,5-dihydrothien-3-yl | 0 | H | $C_2H_5$ | $CH_2-CH=CH_2$ | |
| 22 | 2,5-dihydrothien-3-yl | 0 | H | $C_2H_5$ | $C_2H_5$ | |
| 23 | 1-oxotetrahydrothien-3-yl | 1 | H | n-$C_3H_7$ | $C_2H_5$ | |
| 24 | 1-oxotetrahydrothien-3-yl | 1 | H | n-$C_3H_7$ | $CH_2-CH=CH_2$ | |
| 25 | 1-oxotetrahydrothien-3-yl | 1 | H | $C_2H_5$ | $CH_2-CH=CH_2$ | |
| 26 | 1-oxotetrahydrothien-3-yl | 1 | H | $C_2H_5$ | $C_2H_5$ | |
| 27 | 1,1-dioxotetrahydrothien-3-yl | 1 | H | n-$C_3H_7$ | $C_2H_5$ | |
| 28 | 1,1-dioxotetrahydrothien-3-yl | 1 | H | n-$C_3H_7$ | $CH_2CH=CH_2$ | |
| 29 | 1,1-dioxotetrahydrothien-3-yl | 1 | H | $C_2H_5$ | $CH_2CH=CH_2$ | |
| 30 | 1,1-dioxotetrahydrothien-3-yl | 1 | H | $C_2H_5$ | $C_2H_5$ | |
| 31 | 2-methyl-tetrahydrothien-3-yl | 0 | H | n-$C_3H_7$ | $C_2H_5$ | 0.97(t,3H); 3.25(m,1H); 4.10(q,2H) |
| 32 | 2-methyl-tetrahydrothien-3-yl | 0 | H | n-$C_3H_7$ | $CH_2-CH=CH_2$ | 0.97(t,3H); 1.34(d,3H); 3.24(m,1H); 4.53(d,2H) |
| 33 | 2-methyl-tetrahydrothien-3-yl | 0 | H | $C_2H_5$ | $CH_2-CH=CH_2$ | |
| 34 | 2-methyl-tetrahydrothien-3-yl | 0 | H | $C_2H_5$ | $C_2H_5$ | |
| 35 | 2,2-dimethyltetrahydrothien-3-yl | 0 | $COOCH_3$ | n-$C_3H_7$ | $C_2H_5$ | |
| 36 | 2,2-dimethyltetrahydrothien-3-yl | 0 | $COOCH_3$ | n-$C_3H_7$ | $CH_2-CH=CH_2$ | |
| 37 | 2,2-dimethyltetrahydrothien-3-yl | 0 | H | n-$C_3H_7$ | $C_2H_5$ | 0.98(t,3H); 1.36(s,3H); 1.52(s,3H); 4.10(q,2H) |
| 38 | 2,2-dimethyltetrahydrothien-3-yl | 0 | H | n-$C_3H_7$ | $CH_2-CH=CH_2$ | 0.97(t,3H); 1.36(s,3H); 1.52(s,3H); 4.53(d,2H) |
| 39 | 2,2-dimethyltetrahydrothien-3-yl | 0 | H | $C_2H_5$ | $CH_2-CH=CH_2$ | 1.16(t,3H); 1.35(s,3H); 1.52(s,3H); 4.54(d,2H) |
| 40 | 2,2-dimethyltetrahydrothien-3-yl | 0 | | $C_2H_5$ | $C_2H_5$ | 1.16(t,3H); 1.36(s,3H); 1.52(s,3H); 4.13(q,2H) |
| 41 | 2,2-dimethyl-2,5-dihydrothien-3-yl | 0 | H | n-$C_3H_7$ | $C_2H_5$ | 1.51(s,6H); 3.68(d,2H); 4.15(q,2H); 5.63(t,1H) |
| 42 | 2,2-dimethyl-2,5-dihydrothien-3-yl | 0 | H | n-$C_3H_7$ | $CH_2-CH=CH_2$ | 1.51(s,6H); 3.65(d,2H); 4.55(d,2H); 5.95(m,1H) |
| 43 | 2,2-dimethyl-2,5-dihydrothien-3-yl | 0 | H | $C_2H_5$ | $CH_2-CH=CH_2$ | |
| 44 | 2,2-dimethyl-2,5-dihydrothien-3-yl | 0 | H | $C_2H_5$ | $C_2H_5$ | |
| 45 | 2,2-dimethyl-2,5-dihydrothien-3-yl | 0 | $COOCH_3$ | n-$C_3H_7$ | $C_2H_5$ | |
| 46 | 2,2-dimethyl-2,5-dihydrothien-3-yl | 0 | $COOCH_3$ | n-$C_3H_7$ | $CH_2-CH=CH_2$ | |
| 47 | 2,2-dimethyl-2,5-dihydrothien-3-yl | 0 | $COOCH_3$ | $C_2H_5$ | $CH_2-CH=CH_2$ | |
| 48 | 2,2-dimethyl-2,5-dihydrothien-3-yl | 0 | $COOCH_3$ | $C_2H_5$ | $C_2H_5$ | |
| 49 | tetrahydrothien-2-yl | 0 | H | n-$C_3H_7$ | $C_2H_5$ | |
| 50 | tetrahydrothien-2-yl | 0 | H | n-$C_3H_7$ | $CH_2-CH=CH_2$ | |
| 51 | tetrahydrothien-2-yl | 0 | H | $C_2H_5$ | $CH_2-CH=CH_2$ | |
| 52 | tetrahydrothien-2-yl | 0 | H | $C_2H_5$ | $C_2H_5$ | |
| 53 | tetrahydrothien-2-yl | 1 | H | n-$C_3H_7$ | $C_2H_5$ | 1.35(t, ); 2.85(m,4H); 3.45(m,1H); 4.10(q,2H) |
| 54 | tetrahydrothien-2-yl | 1 | H | n-$C_3H_7$ | $CH_2-CH=CH_2$ | |
| 55 | tetrahydrothien-2-yl | 1 | H | $C_2H_5$ | $CH_2-CH=CH_2$ | |
| 56 | tetrahydrothien-2-yl | 1 | H | $C_2H_5$ | $C_2H_5$ | |
| 57 | tetrahydrothien-2-yl | 2 | H | n-$C_3H_7$ | $C_2H_5$ | |
| 58 | tetrahydrothien-2-yl | 2 | H | n-$C_3H_7$ | $CH_2-CH=CH_2$ | |

-continued

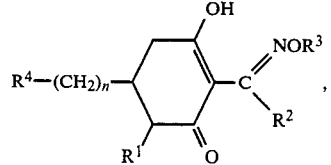

(I)

| No. | R⁴ | n | R¹ | R² | R³ | $^1$H—NMR (ppm) |
|---|---|---|---|---|---|---|
| 59 | tetrahydrothien-2-yl | 2 | H | $C_2H_5$ | $CH_2-CH=CH_2$ | |
| 60 | tetrahydrothien-2-yl | 2 | H | $C_2H_5$ | $C_2H_5$ | |
| 61 | 1-oxotetrahydrothien-2-yl | 1 | H | $n-C_3H_7$ | $C_2H_5$ | 0.95(t,3H); 1.35(t,3H); 1.45–3.50(18H); 4.05(q,2H) |
| 62 | 1-oxotetrahydrothien-2-yl | 1 | H | $n-C_3H_7$ | $CH_2-CH=CH_2$ | |
| 63 | 1-oxotetrahydrothien-2-yl | 1 | H | $C_2H_5$ | $CH_2-CH=CH_2$ | |
| 64 | 1-oxotetrahydrothien-2-yl | 1 | H | $C_2H_5$ | $C_2H_5$ | |
| 65 | 1-oxotetrahydrothien-2-yl | 2 | H | $n-C_3H_7$ | $C_2H_5$ | |
| 66 | 1-oxotetrahydrothien-2-yl | 2 | H | $n-C_3H_7$ | $CH_2-CH=CH_2$ | |
| 67 | 1-oxotetrahydrothien-2-yl | 2 | H | $C_2H_5$ | $CH_2-CH=CH_2$ | |
| 68 | 1-oxotetrahydrothien-2-yl | 2 | H | $C_2H_5$ | $C_2H_5$ | |
| 69 | 1-oxotetrahydrothien-2-yl | 1 | H | $n-C_3H_7$ | $C_2H_5$ | |
| 70 | 1-oxotetrahydrothien-2-yl | 1 | H | $n-C_3H_7$ | $CH_2-CH=CH_2$ | |
| 71 | 1-oxotetrahydrothien-2-yl | 1 | H | $C_2H_5$ | $CH_2-CH=CH_2$ | |
| 72 | 1-oxotetrahydrothien-2-yl | 1 | H | $C_2H_5$ | $C_2H_5$ | |
| 73 | 1,1-dioxotetrahydrothien-2-yl | 2 | H | $n-C_3H_7$ | $C_2H_5$ | |
| 74 | 1,1-dioxotetrahydrothien-2-yl | 2 | H | $n-C_3H_7$ | $CH_2-CH=CH_2$ | |
| 75 | 1,1-dioxotetrahydrothien-2-yl | 2 | H | $C_2H_5$ | $CH_2-CH=CH_2$ | |
| 76 | 1,1-dioxotetrahydrothien-2-yl | 2 | H | $C_2H_5$ | $C_2H_5$ | |
| 77 | 4,5-dihydro-4-methylthien-2-yl | 0 | H | $C_3H_7$ | $C_2H_5$ | |
| 78 | 4,5-dihydro-4-methylthien-2-yl | 0 | H | $C_3H_7$ | $CH_2-CH=CH_2$ | |
| 79 | 4,5-dihydro-4-methylthien-2-yl | 0 | H | $C_2H_5$ | $CH_2-CH=CH_2$ | |
| 80 | 4,5-dihydro-4-methylthien-2-yl | 0 | H | $C_2H_5$ | $C_2H_5$ | |
| 81 | 4,5-dihydro-4,5-dimethylthien-2-yl | 0 | H | $n-C_3H_7$ | $C_2H_5$ | |
| 82 | 4,5-dihydro-4,5-dimethylthien-2-yl | 0 | H | $n-C_3H_7$ | $CH_2-CH=CH_2$ | |
| 83 | 4,5-dihydro-4,5-dimethylthien-2-yl | 0 | H | $C_2H_5$ | $CH_2-CH=CH_2$ | |
| 84 | 4,5-dihydro-4,5-dimethylthien-2-yl | 0 | H | $C_2H_5$ | $C_2H_5$ | |
| 85 | 4,5-dimethyltetrahydrothien-2-yl | 0 | H | $n-C_3H_7$ | $C_2H_5$ | |
| 86 | 4,5-dimethyltetrahydrothien-2-yl | 0 | H | $n-C_3H_7$ | $CH_2-CH=CH_2$ | |
| 87 | 4,5-dimethyltetrahydrothien-2-yl | 0 | H | $C_2H_5$ | $CH_2-CH=CH_2$ | |
| 88 | 4,5-dimethyltetrahydrothien-2-yl | 0 | H | $C_2H_5$ | $C_2H_5$ | |
| 89 | 4,5-dihydro-4-ethyl-5-propylthien-2-yl | 0 | H | $n-C_3H_7$ | $C_2H_5$ | |
| 90 | 4,5-dihydro-4-ethyl-5-propylthien-2-yl | 0 | H | $n-C_3H_7$ | $CH_2-CH=CH_2$ | |
| 91 | 4,5-dihydro-4-ethyl-5-propylthien-2-yl | 0 | H | $C_2H_5$ | $CH_2-CH=CH_2$ | |
| 92 | 4,5-dihydro-4-ethyl-5-propylthien-2-yl | 0 | H | $C_2H_5$ | $C_2H_5$ | |
| 93 | 4-ethyl-5-propyltetrahydrothien-2-yl | 0 | H | $n-C_3H_7$ | $C_2H_5$ | |
| 94 | 4-ethyl-5-propyltetrahydrothien-2-yl | 0 | H | $n-C_3H_7$ | $CH_2-CH=CH_2$ | |
| 95 | 4-ethyl-5-propyltetrahydrothien-2-yl | 0 | H | $C_2H_5$ | $CH_2-CH=CH_2$ | |
| 96 | 4-ethyl-5-propyltetrahydrothien-2-yl | 0 | H | $C_2H_5$ | $C_2H_5$ | |
| 97 | 2,5-dihydrothien-3-yl | 0 | $COOCH_3$ | $n-C_3H_7$ | $C_2H_5$ | 1.00(t,3H); 1.32(t,3H); 4.11(q,2H); 5.68(t,1H) |
| 98 | 2-methyl-2,5-dihydrothien-3-yl | 0 | H | $n-C_3H_7$ | $C_2H_5$ | 0.99(t,3H); 1.34(t,3H); 4.09(q,2H); 5.51(t,1H) |
| 99 | 2,2-dimethyl-2,5-dihydrothien-3-yl | 0 | H | $n-C_3H_7$ | $CH_2-CH=CHCl$ (trans) | 0.98(t,3H); 1.61(s,6H); 4.51(d,2H); 5.60(t,1H) |
| 100 | 1,1-dioxo-tetrahydrothien-2-yl | 1 | H | $n-C_3H_7$ | $C_2H_5$ | 0.98(t,3H); 1.17(t,3H); 3.09(m,3H); 4.05(q,2H) |

The cyclohexenone derivatives of the formula I and their salts may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isoocttylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingedient.

Examples of formulations are give below.

I. 90 parts by weigh of compound no. 1 is mixed with 10 parts by weight of N-methyl-alpha-pyrrolidone. A mixture is obtained which is suitable for application in the form of very fine drops.

II. 20 parts by weight of compound no. 53 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 41 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 19 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 53 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 41 parts of the calcium salt of dodecylbenzene-sulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 4 kg/ha, but is preferably from 0.1 to 3 kg/ha.

The action of the cyclohexenone derivatives of the formula I on the growth of plants from the Gramineae family and broadleaved crop plants is demonstrated in greenhouse experiments.

The vessels employed were plastic flowerpots having a volume of 300 cm³, and which were filled with a sandy loam containing about 3.0% humus. For the preemergence treatment, the active ingredients were applied to the surface of the soil immediately after the seeds had been sown. The compounds were emulsified or supended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment.

The application rate for postemergence treatment was 0.06 kg of active ingredient per hectare. No covers were placed on vessels in this treatment method.

The pots were set up in the greenhouse-species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Avena sativa, Echinochloa crusgalli, Lolium multiflorum, Setaria italica, Sinapis alba,* and *Triticum aestivum.*

The compounds 2-(1-ethoxyaminobutylidene)-5-(tetrahydrofuran-3-yl)-cyclohexane-1,3-dione (A) and 2-(1-ethoxyaminobutylidene)-5-(tetrahydrofuran-2-yl)-cyclohexane-1,3-dione (B) disclosed in European Laid-Open Application 00 71 707 were used as comparative agents.

The application rates for the comparative agents were the same as those for the compounds according to the invention.

On preemergence application, for instance compounds nos. 1, 19 and 41 (at 3.0 kg/ha) proved to be herbicidally effective on plants from the Gramineae family. *Sinapis alba,* as broadleaved test plant, remained undamaged.

Grasses selected by way of exaple, such as *Avena fatua, Alopecurus myosuroides* and *Setaria italica,* were combatted well by 0.06 kg/ha of compounds nos. 41 and 53 (applied postemergence). The advantage of these compounds over prior art cyclohexenone derivatives is that in spite of this herbicidal action—achieved postemergence—on Gramineae, the crop plant wheat from the same family is not damaged. In contrast to comparative agents A and B, the compounds according to the invention are thus selective in this crop.

In view of the numerous application methods possible, the compounds according to the invention may be used in a further large number of crops for removing unwanted wild grasses or grassy crop plants growing where they are not desired.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |

-continued

| Botanical name | Common name |
|---|---|
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I and their salts may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamtes, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

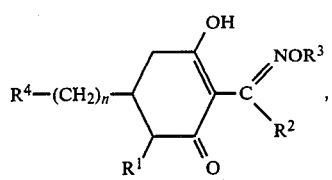

where $R^1$ is hydrogen or alkoxycarbonyl of 2 to 5 carbon atoms, $R^2$ is alkyl of 1 to 4 carbon atoms, $R^3$ is alkyl of 1 to 4 carbon atoms, alkenyl of 3 or 4 carbon atoms, alkynyl of 3 or 4 carbon atoms or haloalkenyl of 3 or 4 carbon atoms and 1 to 3 halogen atoms, $R^4$ is a tetrahydrothienyl or dihydrothienyl or said groups in which the sulfur atom is replaced by sulfinyl or sulfonyl group as a ring member and is unsubstituted or substituted by 1, 2 or 3 alkyl groups of 1 to 4 carbon atoms, and n is 0 or 1, with the proviso that n is not 0 when $R^4$ is a 5-membered ring containing a sulfinyl or sulfonyl group, and salts thereof.

2. A cyclohexenone derivative of the formula I as set forth in claim 1 where $R^1$ is hydrogen.

3. A cyclohexenone derivative of the formula I as set forth in claim 1, where n is 0 and $R^4$ is tetrahydrothienyl.

4. A cyclohexenone derivative of the formula I as set forth in claim 1, where $R^1$ is hydrogen, $R^2$ is n-propyl, $R^3$ is ethyl, $R^4$ is tetrahydrothien-2-yl and n is 1.

5. A herbicide containing inert additives and a herbicidally effective amount of a cyclohexenone derivative of the formula I as set forth in claim 1, or a salt thereof.

6. A herbicide as set forth in claim 5, containing from 0.1 to 95 wt% of a cyclohexenone derivative of the formula I.

7. A herbicide containing inert additives and a herbicidally effective amount of a cyclohexenone derivative of the formula I as set forth in claim 2, or a salt thereof.

8. A herbicide containing inert additives and a herbicidally effective amount of a cyclohexenone derivative of the formula I as set forth in claim 3, or a salt thereof.

9. A process for combatting the growth of unwanted plants, wherein the unwanted plants and/or the area to be kept free from unwanted plant growth are treated with a herbicidally effective amount of a cyclohexenone derivative of the formula I as set forth in claim 1, or a salt thereof.

10. A cyclohexenone derivative of the formula I as set forth in claim 1, wherein $R^1$ is hydrogen, $R^2$ isn-propyl, $R^3$ is ethyl, $R^4$ is tetrahydrothienyl and n is 0.

11. A cyclohexenone derivative of the formula I as set forth in claim 1, wherein $R^1$ is hydrogen, $R^2$ is n-propyl, $R^3$ is ethyl, $R^4$ is dihydrothienyl and n is 0.

12. A cyclohexenone derivative of the formula I as set forth in claim 1, wherein $R^1$ is hydrogen, $R^2$ is n-propyl, $R^3$ is ethyl, $R^4$ is 2,2-dimethyl-2,5-dihyrothien-3-yl and n is 0.

13. A cyclohexenone derivative of the formula I as set forth in claim 1, wherein $R^1$ is hydrogen, $R^2$ is n-propyl, $R^3$ is ethyl, $R^4$ is tetrahydrothienyl and n is 1.

14. The process of claim 9, wherein the unwanted plants are located among wheat.

* * * * *